United States Patent
Matsui et al.

(10) Patent No.: US 6,194,164 B1
(45) Date of Patent: *Feb. 27, 2001

(54) METHOD FOR QUANTITATING CHOLESTEROL PRESENT IN LOW DENSITY LIPOPROTEINS

(75) Inventors: Hiroshi Matsui; Kazushige Mizuno; Yasuki Ito; Shuichi Ohara; Akira Fujiwara; Kenichi Takasugi, all of Goshen; Masahiko Okada, Niigata, all of (JP)

(73) Assignee: Denka Seiken Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/402,880
(22) PCT Filed: Oct. 13, 1997
(86) PCT No.: PCT/JP97/03663
  § 371 Date: Oct. 14, 1999
  § 102(e) Date: Oct. 14, 1999
(87) PCT Pub. No.: WO98/47005
  PCT Pub. Date: Oct. 22, 1998

(30) Foreign Application Priority Data

Apr. 14, 1997 (JP) .................................... 9-111944

(51) Int. Cl.$^7$ .............. C12Q 1/60; C12Q 1/44; C12Q 1/26; C12Q 1/28
(52) U.S. Cl. .................. 435/11; 435/19; 435/25; 435/27; 435/28
(58) Field of Search ............. 435/11, 19, 25, 435/27, 28

(56) References Cited

U.S. PATENT DOCUMENTS 5,807,696  9/1998  Miyauchi et al. .............. 435/11

FOREIGN PATENT DOCUMENTS

| 0676642 A1 | 10/1995 | (EP) . |
| 0764848 A1 | 3/1996 | (EP) . |
| 7501945 | 3/1995 | (JP) . |
| 730136 | 11/1995 | (JP) . |
| 9299 | 1/1997 | (JP) . |
| WO 9628734 | 9/1996 | (WO) . |
| WO 974553A1 | 12/1997 | (WO) . |

OTHER PUBLICATIONS

Miki, Yutaka; Seibutsu Shiryo Buneski, vol. 21(5), pp. 379–384 (Abstract Only), 1998.*

* cited by examiner

Primary Examiner—Louise N. Leary
(74) Attorney, Agent, or Firm—Birch, Stewart, Kolasch & Birch, LLP

(57) ABSTRACT

A method for quantifying LDL cholesterol, by which LDL cholesterol is separately quantified simply without requiring complicated centrifuge operation is disclosed. The method for quantifying cholesterol in low density lipoprotein according to the present invention comprises a first step of erasing cholesterol in high density lipoprotein, very low density lipoprotein and chylomicron in a test sample, and a second step of quantifying cholesterol remaining in the test sample.

13 Claims, 2 Drawing Sheets

METHOD FOR QUANTITATING CHOLESTEROL PRESENT IN LOW DENSITY LIPOPROTEINS

This application is the national phase under 35 U.S.C. §371 of prior PCT International Application No. PCT/JP97/03663 which has an International filing date of Oct. 13, 1997 which designated the United States of America.

TECHNICAL FIELD

The present invention relates to a method for quantifying cholesterol in low density lipoprotein (LDL, The cholesterol in low density lipoprotein will be hereinafter also referred to as "LDL cholesterol". In the present specification, the term "cholesterol" includes both ester type cholesterol and free cholesterol), which is important for the diagnosis of arterial sclerosis.

BACKGROUND ART

LDL plays a main role in transportation of cholesterol in blood and most of the cholesterol deposited on the blood vessel wall in pultaceous arterial sclerosis is originated from LDL. Increase in the amount of LDL in plasma is one of the major risk factors in pultaceous sclerosis such as ischemic heart disease, so that separate quantification of LDL cholesterol is clinically important.

Conventional methods for quantifying LDL cholesterol include a method comprising two steps, that is, a fractionation operation and an operation for quantifying the cholesterol, and a method in which the blood levels of total cholesterol, HDL cholesterol and triglyceride are determined and the amount of the LDL cholesterol is determined according to the Friedewald's equation.

Fractionation operation includes ultracentrifugation method, precipitation method, immunochemical method and the like. In the ultracentrifugation method, LDL is separated exploiting the difference in the specific gravity by an ultracentrifuge, and the amount of the cholesterol therein is measured. In the precipitation method, anti-HDL antibody, polyanion and a divalent cation are added to form an insoluble precipitate, and the LDL cholesterol in the supernatant after centrifugation is quantified (WPI Acc No.85-116848/20). In the immunochemical method, anti-HDL antibody, anti-VLDL antibody and anti-CM antibody are bound to latex particles, and the latex particles are removed by centrifugation or by passing through a filter after agglutination, followed by quantifying the LDL cholesterol (WPI Acc No. 84-301275/49). However, these conventional methods are problematic in simplicity or cost.

According to the Friedewald's equation, the amount of LDL cholesterol is calculated by subtracting the amount of the HDL cholesterol from the amount of the total cholesterol, and then further subtracting the ⅕ of the amount of the triglyceride. However, since this method does not take the influence by the diet and the individual difference, this method is problematic in accuracy.

Recently, a method for quantification of LDL cholesterol, which does not require fractionation operation, has been reported (WPI Acc No. 83-766269/38). However, in this method, the specificity to LDL is not sufficient.

DISCLOSURE OF THE INVENTION

The object of the present invention is to provide a method for quantifying LDL cholesterol, by which LDL cholesterol is separately quantified simply without requiring complicated centrifuge operation.

The present inventors discovered that the amount of cholesterol in LDL can be quantified by erasing the cholesterol other than the cholesterol in the low density lipoprotein in the first step, and by measuring the remaining cholesterol in the subsequent second step, thereby completing the present invention.

That is, the present invention provides a method for quantifying cholesterol in low density lipoprotein in a test sample which may contain low density lipoprotein, high density lipoprotein, very low density lipoprotein and/or chylomicron, which method comprises a first step of erasing cholesterol in high density lipoprotein, very low density lipoprotein and chylomicron in a test sample, and a second step of quantifying cholesterol remaining in said test sample.

By the present invention, a method for quantifying LDL cholesterol, by which LDL cholesterol is separately quantified simply without requiring complicated centrifuge operation, was provided.

BEST MODE FOR CARRYING OUT THE INVENTION

Figure 1:
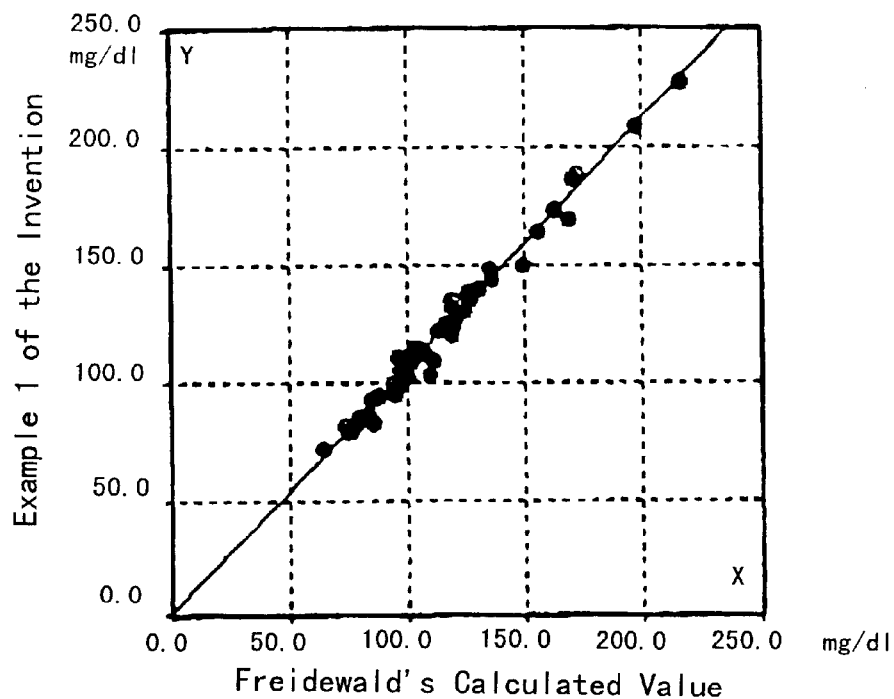
FIG. 1 shows the correlation between the results of the measurement of the LDL cholesterol in Example 1 and the amount calculated by the Friedewald's equation.

Cholesterol contained in lipoproteins includes ester type cholesterol (cholesterol ester) and free cholesterol. In this specification, the term "cholesterol" includes both of these unless otherwise specified.

The test sample subjected to the method of the present invention may be any sample which may contain lipoproteins such as HDL, LDL, VLDL and CM. Examples of the test samples include body fluids such as blood, sera and plasma as well as dilutions thereof, although the test samples are not restricted thereto.

The method of the present invention comprises a first step and a second step. In the first step, the cholesterol in HDL, VLDL and CM in the test sample is erased, and in the second step, the cholesterol remaining in the test sample is quantified. Since the cholesterol in HDL, VLDL and CM is erased in the first step, the cholesterol quantified in the second step is mainly the cholesterol in LDL in the test sample.

The term "erase" in the first step herein means to decompose the cholesterol and to make the decomposed products undetectable in the subsequent second step. The methods for selectively erasing the cholesterol in the lipoproteins other than LDL, that is, in HDL, VLDL, CM and the like include the following methods.

That is, cholesterol esterase and cholesterol oxidase are made to act on the test sample in the presence of a surfactant which acts on lipoproteins other than low density lipoprotein, and the generated hydrogen peroxide is erased.

Methods for erasing hydrogen peroxide include a method in which the hydrogen peroxide is decomposed to water and oxygen by catalase; and a method in which a phenol-based or an aniline-based hydrogen donor compound is reacted with the hydrogen peroxide to convert the hydrogen peroxide to a colorless quinone, although the methods for removing hydrogen peroxide are not restricted to these methods.

The concentration of the cholesterol esterase in the reaction mixture in the first step may preferably be about 0.2 to 1.0 U/ml, and the cholesterol esterase may preferably be originated from a bacterium belonging to the genus Pseudomonas. The concentration of the cholesterol oxidase may preferably be about 0.1 to 0.7 U/ml, and the cholesterol oxidase may preferably be originated from a bacterium or yeast. The concentration of the catalase may preferably be about 40 to 100 U/ml and the concentration of the peroxidase by which the hydrogen peroxide is converted to a colorless quinone may preferably be about 0.4 to 1.0 U/ml. The concentration of the phenol-based or aniline-based hydrogen donor compound may preferably be about 0.4 to 0.8 mmol/l.

Preferred surfactants which act on the lipoproteins other than LDL, which are used in the first step, include polyalkylene oxide derivatives having HLB values of not less than 13 and not more than 15, preferably not less than 13 and not more than 14. Examples of the derivatives here include condensation products with higher alcohols, condensation products with higher fatty acids, condensation products with higher fatty acid amides, condensation products with higher alkylamines, condensation products with higher alkylmercaptane and condensation products with alkyl phenols. The method for calculating HLB of surfactants is well-known, and is described in, for example, Hiroshi HORIUCHI, "New Surfactants", 1986, Sankyo Shuppan.

Preferred specific examples of the polyalkylene oxide derivatives having HLB values of not less than 13 and not more than 15 include polyoxyethylene lauryl ether, polyoxyethylene cetyl ether, polyoxyethylene oleyl ether, polyoxyethylene higher alcohol ether, polyoxyethylene octyl phenyl ether, polyoxyethylene nonylphenyl ether and the like, of which HLB value is not less than 13 and not more than 15, although the surfactant is not restricted thereto.

As the surfactant used in the first step, a cation surfactant may also be used. In this case, as the cation surfactant, those having the quaternary ammonium salt as a hydrophilic group, represented by the following formula (I), are preferred.

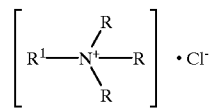

(I)

wherein R independently represents $C_1$–$C_8$ linear alkyl group and $R^1$ represents $C_3$–$C_{20}$ alkenyl group.

The concentration of the above-mentioned surfactants used in the first step may preferably be about 0.1 to 10 g/l, more preferably about 0.5 to 5.0 g/l.

The reaction in the first step may preferably be carried out in a buffer with a pH of 5 to 8, and the buffer may preferably be one containing an amine such as Tris buffer, triethanolamine or Good's buffer. Especially, Bis-Tris, PIPES, MOPSO, BES, HEPES and POPSO which are Good's buffer are preferred. The concentration of the buffer may preferably be about 10 to 500 mM.

To inhibit the reaction with LDL and to increase the degree of erasing of the other lipoproteins, a divalent metal ion may be contained in the reaction mixture. Preferred examples of the divalent metal ion include copper ion, iron ion and magnesium ion. Among these, magnesium ion is especially preferred. The concentration of the divalent metal ion may preferably be about 5 to 200 mM.

A lipoproteinase may optionally be added to the reaction mixture in the first step. Addition of this enzyme is preferred because especially the cholesterol in VLDL easily reacts. The concentration of this enzyme in the reaction mixture may preferably be about 5.0 to 10.0 U/ml.

The reaction temperature in the first step may preferably be about 25° C. to 40° C., and 37° C. is best preferred. The reaction time may be about 2 to 10 minutes.

In the subsequent second step, the cholesterol remaining in the test sample is quantified. This may be carried out by, for example, adding a surfactant which acts on at least LDL and quantifying the hydrogen peroxide by the action of the cholesterol esterase and the cholesterol oxidase added in the first step. Here, the surfactant which acts on at least LDL may be a surfactant which selectively acts on LDL alone or may be a surfactant which acts on all lipoproteins.

Preferred examples of the surfactant which acts on all lipoproteins include polyalkylene oxide derivatives having HLB values of not less than 11 and not more than 13, preferably not less than 12 and not more than 13. Examples of the derivatives here include condensation products with higher alcohols, condensation products with higher fatty acids, condensation products with higher fatty acid amides, condensation products with higher alkylamines, condensation products with higher alkylmercaptane and condensation products with alkyl phenols.

Preferred specific examples of the polyalkylene oxide derivatives having HLB values of not less than 11 and not more than 13 include polyoxyethylene lauryl ether, polyoxyethylene cetyl ether, polyoxyethylene oleyl ether, polyoxyethylene higher alcohol ether, polyoxyethylene octyl phenyl ether, polyoxyethylene nonylphenyl ether and the like, of which HLB value is not less than 11 and not more than 13, although the surfactant is not restricted thereto.

Examples of the surfactants which selectively act on LDL alone include anion surfactants. Although the anion surfactants used here are not restricted, those having one or more aromatic rings to which one or more $C_4$–$C_{18}$ linear or branched alkyl groups are attached are preferred. Here, the aromatic ring may preferably be those consisting of carbon atoms and hydrogen atoms, such as benzene, naphthalene and diphenyl. Those in which one or more hydrophilic groups such as sulfonate group are attached to the above-mentioned aromatic ring are further preferred. Preferred examples of such anion surfactants include those represented by the following formulae (II) to (VI).

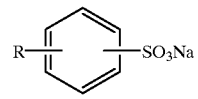

(II)

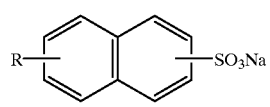

(III)

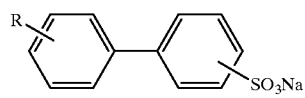

(IV)

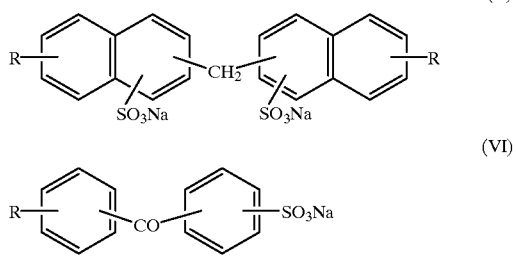

(V)

(VI)

In formulae (II) to (VI), R independently represents $C_4$–$C_{18}$ linear or branched alkyl group. Preferred examples of the anion surfactants which may be used in the second step also include higher alcohol sodium sulfate and the like.

The concentration of the surfactant used in the second step may preferably be about 0.1 to 100 g/l, more preferably about 1 to 50 g/l.

Other preferred reaction conditions in the second step are the same as the preferred reaction conditions in the first step.

The present invention will now be described more concretely by way of examples thereof. It should be noted, however, the present invention is not restricted to the examples below.

EXAMPLE 1

| First Reagents | |
|---|---|
| BES buffer, pH 6.0 | 100 mmol/l |
| HDAOS: N-(2-hydroxysulfopropyl)-3,5-dimethyoxy-aniline | 0.7 mmol/l |
| Cholesterol esterase originated from a bacterium belonging to the genus Pseudomonas (trademark "CEN" commercially available from Asahi Chemical Industry Co. Ltd.) | 0.8 U/ml |
| Cholesterol oxidase originated from a bacterium belonging to the genus Streptomyces (trademark "COO" commercially available from Toyobo Co. Ltd.) | 0.5 U/ml |
| Catalase | 80 U/ml |
| Magnesium chloride | 10 mmol/l |
| Emulgen B66 commercially available from KAO CORPORATION (polyoxyethylene derivative (HLB = 13.2)) | 0.2% |
| Second Reagents | |
| BES buffer, pH 7.0 | 50 mmol/l |
| 4-aminoantipyrine | 4.0 mmol/l |
| Peroxidase | 2.4 U/ml |
| Sodium azide | 0.1% |
| Emulgen A60 commercially available from KAO CORPORATION (polyoxyethylene derivative (HLB = 12.8)) | 5.0% |

To each of 4 samples having a volume of 4 µl containing purified HDL, LDL, VLDL and CM at a concentration of 100 mg/dl in terms of cholesterol, respectively, 300 µl of the above-described first reagents which had been preliminarily warmed at 37° C. were added and each of the resulting mixtures was allowed to react at 37° C. for 5 minutes. Thereafter, 100 µl of the second reagents were added to each mixture and each of the resultants was allowed to react for 5 minutes, followed by measurement of absorbance of each reaction mixture at 600 nm. Based on the measured absorbances, the amounts of cholesterol were calculated and the ratio of the thus calculated amount to the amount of the cholesterol in the sample was calculated, which is defined as capture ratio. The results are shown in Table 1 below.

TABLE 1

| | Capture Ratio | | | |
|---|---|---|---|---|
| CM | VLDL | LDL | HDL |
| <1.0% | <5.0% | 70.0% | <1.0% |

As shown in Table 2, by the above-described method, most of the cholesterol in LDL was captured while the cholesterol in other lipoproteins was not substantially captured, so that the cholesterol in LDL can be selectively quantified.

EXAMPLE 2

| First Reagents | |
|---|---|
| PIPES buffer, pH 7.0 | 50 mmol/l |
| HDAOS | 0.7 mmol/l |
| Cholesterol esterase originated from a bacterium belonging to the genus Pseudomonas (trademark "CEN" commercially available from Asahi Chemical Industry Co. Ltd.) | 0.8 U/ml |
| Cholesterol oxidase originated from a bacterium belonging to the genus Streptomyces (trademark "COO" commercially available from Toyobo Co. Ltd.) | 0.5 U/ml |
| Catalase | 80 U/ml |
| Magnesium chloride | 10 mmol/l |
| Emulgen B66 commercially available from KAO CORPORATION | 0.2% |
| Second Reagents | |
| PIPES buffer, pH 7.0 | 50 mmol/l |
| 4-aminoantipyrine | 4.0 mmol/l |
| Peroxidase | 2.4 U/ml |
| Sodium azide | 0.1% |
| Triton X100 | 3.0% |

The same procedures as in Example 1 were repeated and the reactivity with each lipoprotein was measured. The results are shown in Table 2 below.

TABLE 2

| | Capture Ratio | | | |
|---|---|---|---|---|
| CM | VLDL | LDL | HDL |
| <1.0% | <5.0% | 71.0% | <1.0% |

EXAMPLE 3

Using sera of normal persons as test samples, the procedures in Examples 1 or 2 were repeated to measure the concentrations of LDL cholesterol. As controls, the concentrations of LDL cholesterol in the sera were measured employing the Friedewald's equation (CLIN. CHEM., 41, 1414, 1995). The results are shown in FIGS. 1 and 2 showing the correlation therebetween.

Figure 2:
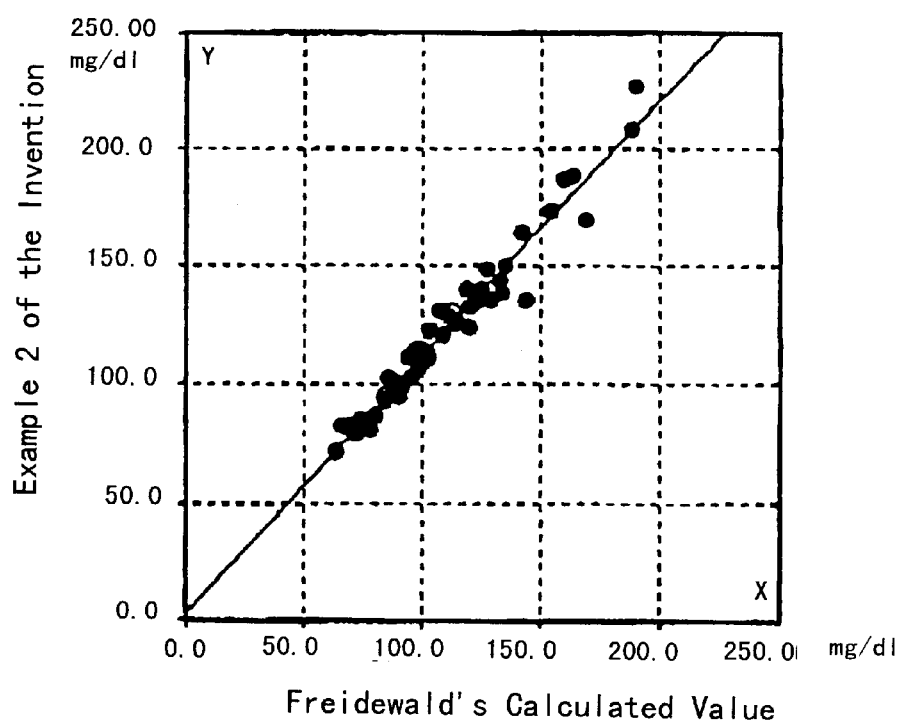
FIG. 2 shows the correlation between the results of the measurement of the LDL cholesterol in Example 2 and the amount calculated by the Friedewald's equation.

As shown in FIGS. 1 and 2, the results of measurement by the both methods well agreed, so that it was proved that the cholesterol in LDL can be quantified accurately by the method of the present invention.

EXAMPLE 4

| First Reagents | |
|---|---|
| Good's buffer, pH 7.0 | 50 mmol/l |
| HDAOS | 0.7 mmol/l |
| Cholesterol esterase | 0.8 U/ml |
| Cholesterol oxidase | 0.5 U/ml |
| Catalase | 80 U/ml |
| Cation surfactant (lauryl trimethylammonium chloride) | 0.1% |
| Second Reagents | |
| 4-aminoantipyrine | 4.0 mmol/l |
| Peroxidase | 2.4 U/ml |
| Sodium azide | 0.1% |
| Nonionic surfactant (polyoxyethylene lauryl ether) | 0.1% |

(The nonionic surfactant was used in the second reaction.)

Twenty microliters of a sample was mixed with 180 μl of the first reagents preliminarily warmed at 37° C. and the resulting mixture was allowed to react at 37° C. for 5 minutes. Then 60 μl of the second reagents were added and the resulting mixture was allowed to react at 5 minutes, followed by measurement of the absorbance at 600 nm.

Figure 3:
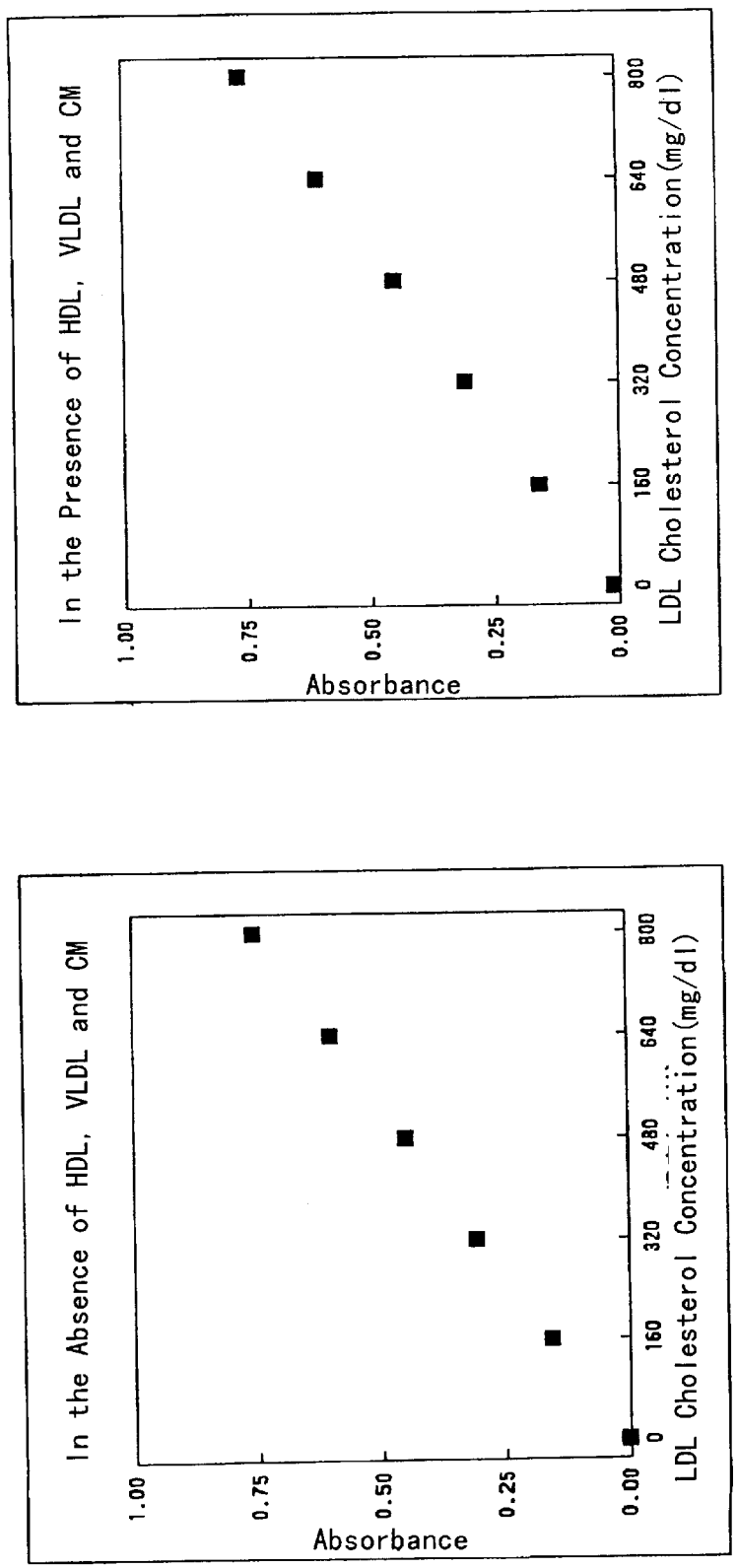
FIG. 3 shows the correlation between the concentration of LDL cholesterol in the absence or presence of HDL, VLDL and CM and the absorbance measured by the present invention in Example 4.

FIG. 3 shows the relationship between the concentration of the LDL cholesterol and the absorbance. As can be seen from FIG. 3, LDL cholesterol can be measured specifically and concentration-dependently even in the presence of HDL, VLDL and CM.

EXAMPLE 5

Using sera as test samples, the same procedures as in Example 4 were repeated to determine the concentration of the LDL cholesterol. As controls, the concentrations of LDL cholesterol in the sera were measured employing the Friedewald's equation (CLIN. CHEM., 41, 1414, 1995). The results are shown in Table 3. As shown in Table 3, the results obtained by the method of the present invention well agreed wit the results calculated according to the Friedewald's equation.

TABLE 3

| Sample | Friedewald | Example 4 |
|---|---|---|
| 1 | 73.0 | 60.1 |
| 2 | 91.0 | 85.8 |
| 3 | 136.4 | 124.0 |
| 4 | 97.7 | 98.0 |
| 5 | 75.2 | 81.8 |
| 6 | 195.7 | 195.4 |
| 7 | 140.5 | 112.9 |
| 8 | 112.8 | 113.2 |
| 9 | 160.6 | 153.5 |
| 10 | 120.4 | 111.1 |

What is claimed is:

1. A method for quantifying cholesterol in low density lipoprotein in a test sample which may contain low density lipoprotein, high density lipoprotein, very low density lipoprotein and/or chylomicron, which method comprises a first step of enzymatically erasing cholesterol in high density lipoprotein, very low density lipoprotein and chylomicron in a test sample, and a second step of quantifying cholesterol remaining in said test sample, wherein said first step is carried out by the action of cholesterol esterase and cholesterol oxidase in the presence of a surfactant which acts on lipoproteins other than the low density lipoprotein, and by eliminating the generated hydrogen peroxide.

2. The method according to claim 1, wherein said second step comprises adding a surfactant which acts on at least the low density lipoprotein, and quantifying the hydrogen peroxide generated by the actions of said cholesterol esterase and cholesterol oxidase.

3. The method according to claim 2, wherein said surfactant which acts on at least the low density lipoprotein is a surfactant which acts on all of the lipoproteins.

4. The method according to any one of claims 1 to 3, wherein said surfactant which acts on lipoproteins other than the low density lipoprotein, which is used in said first step is a polyalkylene oxide derivative having an HLB value of not less than 13 and not more than 15.

5. The method according to claim 3, wherein said surfactant which acts on all of the lipoproteins used in said second step is a polyalkylene oxide derivative having an HLB value of not less than 11 and less than 13.

6. The method according to claim 1, wherein said surfactant which acts on lipoproteins other than the low density lipoprotein, which is used in said first step, is a cationic surfactant.

7. The method according to claim 6, wherein said cationic surfactant has a quaternary ammonium salt.

8. The method according to claim 2, wherein said surfactant which acts on at least the low density lipoprotein, which is used in the second step, is an anionic surfactant.

9. The method according to claim 1, wherein said first step is carried out at a concentration of said surfactant of 0.1 to 10 g/l.

10. The method according to claim 5 or 8, wherein said polyoxyalkylene derivative having an HLB value of not less than 11 and less than 13 or said anionic surfactant used in said second step has a concentration of 1 to 100 g/l.

11. The method according to claim 1, wherein said first and second steps are carried out in a buffer with a pH of 5 to 8.

12. The method according to claim 11, wherein said buffer contains an amine.

13. The method according to claim 1, wherein said first and second steps are carried out at a temperature of 25 to 40° C.

* * * * *